United States Patent
Kumar et al.

(10) Patent No.: US 8,878,013 B1
(45) Date of Patent: Nov. 4, 2014

(54) INBRED MELON LINES ME007 AND ME009

(71) Applicant: Syngenta Participations AG, Basel (CH)

(72) Inventors: Rakesh Kumar, Woodland, CA (US); Alex Wright May, Woodland, CA (US)

(73) Assignee: Syngenta Participations AG, Basel (CH)

( * ) Notice: Subject to any disclaimer, the term of this patent is extended or adjusted under 35 U.S.C. 154(b) by 0 days.

(21) Appl. No.: 14/163,247

(22) Filed: Jan. 24, 2014

(51) Int. Cl.
*A01H 5/10* (2006.01)
*A01H 5/00* (2006.01)
*A01H 4/00* (2006.01)
*A01H 1/02* (2006.01)
*A01H 5/08* (2006.01)

(52) U.S. Cl.
CPC .. *A01H 5/10* (2013.01); *A01H 1/02* (2013.01); *A01H 5/08* (2013.01)
USPC ............ 800/309; 800/260; 800/265; 800/266

(58) Field of Classification Search
None
See application file for complete search history.

(56) References Cited

U.S. PATENT DOCUMENTS 8,618,361 B1   12/2013   Kumar et al.

OTHER PUBLICATIONS

Seminis. Hardrock brochure, downloaded on Apr. 8, 2013. Retrieved from http://www.seminis.com/global/au/SiteCollectionDocuments/Seminis%20Hardrock.pdf.
Syngenta. (2012). Melon Crop Guide, downloaded on Apr. 8, 2013. Retrieved from http://www.syngenta-us.com/seeds/vegetables/melon/Melon_Crop_Guide.pdf.

*Primary Examiner* — Brent T Page
(74) *Attorney, Agent, or Firm* — Karen Magri (57) ABSTRACT

The present invention provides novel melon plants and plant parts, seed, fruit, and tissue culture therefrom. The invention also provides methods for producing a melon plant by crossing the melon plants of the invention with themselves or another melon plant. The invention also provides plants produced from such a crossing as well as plant parts, seed, fruit, and tissue culture therefrom.

30 Claims, 2 Drawing Sheets

FIGURE 1

MELONS (ME009)

FIGURE 2

INBRED MELON LINES ME007 AND ME009

FIELD OF THE INVENTION

This invention is in the field of melon plants, in particular, the invention relates to novel melon plants characterized by non-climacteric fruit ripening, fruit having a high total solids and/or a fruit having a firm flesh.

BACKGROUND OF THE INVENTION

Cantaloupe belongs to the species *Cucumis melo*, designated as *Cucumis melo* var. cantalupensis. *C. melo* is a member of the family Cucurbitaceae, which contains about 90 genera. Cantaloupe goes by a variety of common names, including mushmelon, muskmelon, rockmelon, sweet melon or Persian melon.

Many cantaloupe varieties are climacteric, meaning that fruit ripening is associated with ethylene production, resulting in abscission ("slip") from the vine. Climacteric fruits may abscise from the vine prior to optimal sugar deposition, which may adversely impact taste.

Accordingly, it would be desirable to develop improved melon plants having improved taste, shelf life and/or shipping characteristics.

SUMMARY OF THE INVENTION

In representative embodiments, the present invention provides novel non-climacteric melon plants that produce fruit that are able to remain on the vine longer (i.e., they do not abscise or "slip" from the vine) than a climacteric melon, which may result in improved taste and/or sweetness. In embodiments, the melon plants of the invention are characterized by fruit having a firm flesh. In embodiments, the melon plants of the invention produce fruit having high total soluble solids. In representative embodiments, the melon plants of the invention are characterized by two or more of these characteristics: non-climacteric fruit ripening, a fruit having a firm flesh and/or a fruit having high soluble solids. In further exemplary embodiments, the melon plants of the invention are characterized by fruit having an enhanced sugar (e.g., sucrose) content and/or a sweeter taste and/or having a longer field shelf life and/or post-harvest shelf life.

As one aspect, the invention provides plant parts (including fruit, seed, gametes) and tissue culture of the melon plants of the invention. The invention further encompasses a harvested or processed product, such as a food product, from the melon plants of the invention (e.g., from the fruit). Further provided are methods of producing seed from the melon plants of the invention. Also provided are methods for producing a melon plant comprising crossing a cantaloupe of the invention with itself or with another melon plant. The invention also provides plants and seed produced by such crossing.

According to particular aspects of the invention, there is provided novel cantaloupe cultivars designated ME007 and ME009. Thus, the invention also encompasses the seeds of cantaloupe cultivars ME007 and ME009, the plants of cantaloupe cultivars ME007 and ME009, methods of producing seed from cantaloupe cultivars ME007 and ME009, and methods for producing a melon plant by crossing a cantaloupe of cultivars ME007 and ME009 with itself or another melon plant, methods for producing a melon plant comprising in its genetic material one or more transgenes, and the transgenic melon plants produced by that method. The invention also relates to methods for producing other melon plant derived from any of cantaloupe cultivars ME007 and ME009, and melon plants derived by the use of those methods. The present invention further relates to hybrid melon seed and plants (and parts thereof including fruit) produced by crossing any of cantaloupe cultivars ME007 and ME009 with another melon plant.

In another aspect, the present invention provides regenerable cells for use in tissue culture of cantaloupe cultivars ME007 and ME009. In representative embodiments, the tissue culture is capable of regenerating plants having essentially all of the physiological and morphological characteristics of the foregoing cantaloupe plants, and of regenerating plants having substantially the same genotype as the foregoing cantaloupe cultivars. Non-limiting examples of regenerable cells in such tissue cultures include meristematic cells, cotyledons, hypocotyl, leaves, pollen, embryos, roots, root tips, anthers, pistils, ovules, shoots, stems, petioles, pith, flowers, capsules, and seeds as well as callus and protoplasts derived from any of the foregoing. Still further, the present invention provides plants regenerated from the tissue culture of the invention.

As a further aspect, the invention provides a method of producing melon seed, the method comprising crossing a plant of cantaloupe cultivar ME007 or ME009 with itself or a second melon plant. Optionally, the method further comprises collecting the seed.

Another aspect of the invention provides methods for producing hybrids and other melon plants derived from cantaloupe cultivars ME007 and ME009. Melon plants derived by the use of those methods are also part of the invention as well as plant parts, seed, fruit and tissue culture from such hybrid or derived melon plants.

The invention also relates to methods for producing a melon plant comprising in its genetic material one or more transgenes and to the transgenic melon plant produced by those methods. Also provided are plant parts, seed, fruit and tissue culture from such transgenic melon plants, optionally wherein one or more cells in the plant part, seed, fruit or tissue culture comprise the transgene. The transgene can be introduced via plant transformation or breeding techniques.

In another aspect, the present invention provides for single gene converted plants of cantaloupe cultivars ME007 and ME009. Plant parts, seed, fruit and tissue culture from such single gene converted plants are also contemplated by the present invention. The single transferred gene may be a dominant or recessive allele. In illustrative embodiments, the single transferred gene will confer such traits as male sterility, male fertility, herbicide resistance, insect or pest (e.g., nematode) resistance, modified fatty acid metabolism, modified carbohydrate metabolism, disease resistance (e.g., for bacterial, fungal and/or viral disease), male fertility, enhanced nutritional quality, increased sweetness, increased flavor, improved ripening control, improved salt tolerance, industrial usage or any combination thereof. The single gene may be a naturally occurring melon gene or a transgene introduced through genetic engineering techniques.

The invention further provides methods for developing melon plants in a melon plant breeding program using plant breeding techniques including without limitation recurrent selection, backcrossing, pedigree breeding, restriction fragment length polymorphism enhanced selection, genetic marker enhanced selection, and transformation. Seeds, plants, and parts thereof (including fruit), produced by such breeding methods are also part of the invention.

The invention also provides methods of multiplication or propagation of melon plants of the invention, which can be accomplished using any method known in the art, for example, via vegetative propagation and/or seed.

The invention further provides a method of producing food or feed comprising (a) obtaining a melon plant of the invention, wherein the plant has been cultivated to maturity, and (b) collecting at least one melon fruit from the plant.

Additional aspects of the invention include harvested products and processed products from the melon plants of the invention. A harvested product can be a whole plant or any plant part, as described herein. Thus, in some embodiments, a non-limiting example of a harvested product includes a seed or a fruit (or a part thereof), a leaf, a stem, and the like.

In representative embodiments, a processed product includes, but is not limited to, cut, sliced, ground, pureed, dried, canned, jarred, packaged, frozen and/or heated fruit and/or seeds of the melon plants of the invention, or any other part thereof. In embodiments, a processed product includes a sugar or other carbohydrate, fiber, protein and/or aromatic compound that is extracted, purified or isolated from a plant of the invention. In embodiments, the processed product includes a flour, meal, sauce, salad, or puree containing a plant of the invention, or a part thereof (e.g., the fruit and/or seed).

The seed of the invention can optionally be provided as an essentially homogenous population of seed of a single plant or cultivar. Essentially homogenous populations of seed are generally free from substantial numbers of other seed, e.g., at least about 90%, 95%, 96%, 97%, 98% or 99% pure.

In representative embodiments, the invention provides a seed of a cantaloupe selected from cantaloupe cultivar ME007 or ME009.

As a further aspect, the invention provides a plant of cantaloupe cultivar ME007 or ME009.

As an additional aspect, the invention provides a cantaloupe plant, or a part thereof, having all the physiological and morphological characteristics of a plant of cantaloupe cultivar ME007 or ME009.

As another aspect, the invention provides flesh of the fruit of the melon plants of the invention and a processed product from the fruit, flesh, and/or seed of the inventive melon plants.

As still another aspect, the invention provides a method of producing cantaloupe seed, the method comprising crossing a melon plant of the invention with itself or a second melon plant. The invention also provides seed produced by this method and plants produced by growing the seed.

As yet a further aspect, the invention provides a method for producing a seed of a melon plant derived from cantaloupe ME007 or ME009, the method comprising: (a) crossing a melon plant of cantaloupe ME007 or ME009 with a second melon plant; and (b) allowing seed of a melon plant derived from cantaloupe ME007 or ME009 to form. In embodiments, the method further comprises: (c) selfing the plant grown from the melon seed derived from cantaloupe ME007 or ME009 or crossing it to a second melon plant to yield additional melon seed derived from cantaloupe ME007 or ME009; and (d) growing plants from the additional melon seed derived from cantaloupe ME007 or ME009 of step (c) to yield additional melon plants derived from cantaloupe ME007 or ME009. Optionally, the method comprises: (e) repeating (c) and (d) one or more times (e.g., one to five, one to six, one to seven, one to ten, three to five, three to six, three to seven, three to eight or three to ten times) to generate further derived melon plants. As another option, the method can comprise collecting the seed. The invention also provides seed produced by these methods and plants produced by growing the seed.

As another aspect, the invention provides a method of producing cantaloupe fruit, the method comprising: (a) obtaining a plant of cantaloupe cultivar ME007 or ME009, wherein the plant has been cultivated to maturity; and (b) collecting fruit from the plant. The invention also provides the fruit produced by this method.

Still further, as another aspect, the invention provides a method of vegetatively propagating a plant of cantaloupe cultivar ME007 or ME009, the method comprising: (a) collecting tissue capable of being propagated from a plant of cantaloupe cultivar ME007 or ME009; (b) cultivating the tissue to obtain proliferated shoots; and (c) rooting the proliferated shoots to obtain rooted plantlets. Optionally, the invention further comprises growing plants from the rooted plantlets. The invention also encompasses the plantlets and plants produced by these methods.

As an additional aspect, the invention provides a method of producing a plant derived from cantaloupe cultivar ME007 or ME009 comprising a desired added trait, the method comprising: (a) crossing a first plant of cantaloupe cultivar ME007 or ME009 with a second melon plant that comprises a desired trait to produce $F_1$ progeny; (b) selecting an $F_1$ progeny that comprises the desired trait; (c) crossing the selected $F_1$ progeny with the first plant of cantaloupe ME007 or ME009 to produce backcross progeny; and (d) selecting backcross progeny comprising the desired trait to produce a plant derived from cantaloupe ME007 or ME009 comprising a desired trait. In embodiments, the selected progeny has non-climacteric fruit ripening, produces a fruit with a firm flesh and/or produces a fruit with high soluble solids. In embodiments, the selected progeny comprises all the morphological and physiological characteristics of the first plant of cantaloupe cultivar ME007 or ME009. Optionally, the method further comprises: (e) repeating steps (c) and (d) one or more times in succession (e.g., one to five, one to six, one to seven, one to ten, three to five, three to six, three to seven, three to eight or three to ten times) to produce a plant derived from cantaloupe cultivar ME007 or ME009 comprising a desired trait.

In representative embodiments, the invention also provides a method of producing a plant of cantaloupe ME007 or ME009 comprising a desired added trait, the method comprising introducing a transgene conferring the desired trait into a plant of cantaloupe ME007 or ME009. The transgene can be introduced by transformation methods (e.g., genetic engineering) or breeding techniques. In embodiments, the plant comprising the transgene has non-climacteric fruit ripening, produces a fruit with a firm flesh and/or produces a fruit with high soluble solids. In embodiments, the plant comprising the transgene comprises all the morphological and physiological characteristics of cantaloupe cultivar ME007 or ME009.

The invention also provides melon plants produced by the methods of the invention, wherein the melon plant has the desired added trait as well as seed from such melon plants.

According to the foregoing methods, the desired added trait can be any suitable trait known in the art including, for example, male sterility, male fertility, herbicide resistance, insect or pest (e.g., nematode) resistance, modified fatty acid metabolism, modified carbohydrate metabolism, disease resistance (e.g., for bacterial, fungal and/or viral disease), enhanced nutritional quality, increased sweetness, increased flavor, improved ripening control, improved salt tolerance, industrial usage, or any combination thereof).

In representative embodiments, a transgene conferring herbicide resistance confers resistance to glyphosate, sulfonylurea, imidazolinone, dicamba, glufosinate, phenoxy propionic acid, L-phosphinothricin, cyclohexone, cyclohexanedione, triazine, benzonitrile, or any combination thereof.

In representative embodiments, a transgene conferring insect or pest resistance encodes a *Bacillus thuringiensis* endotoxin.

In representative embodiments, transgenic plants, transformed plants (e.g., using genetic engineering techniques), single gene converted plants, hybrid plants and melon plants derived from cantaloupe cultivars ME007 and ME009 have non-climacteric fruit ripening and/or produce a fruit with a firm flesh and/or high soluble solids. In representative embodiments, transgenic plants, transformed plants, hybrid plants and melon plants derived from cantaloupe cultivars ME007 or ME009 have at least 3, 4, 5, 6, 7, 8, 9, 10 or more of the morphological and physiological characteristics of cantaloupe cultivars ME007 or ME009, respectively (e.g., as described in Tables 1 to 5), or even of all the morphological and physiological characteristics of cantaloupe cultivars ME007 or ME009, respectively, so that said plants are not significantly different for said traits than cantaloupe cultivar ME007 or ME009, respectively, as determined at the 5% significance level when grown in the same environmental conditions; optionally, with the presence of one or more desired additional traits (e.g., male sterility, disease resistance, pest or insect resistance, herbicide resistance, and the like).

The invention also encompasses plant parts, plant material, pollen, ovules, fruit and seed from the melon plants of the invention. Also provided is a tissue culture of regenerable cells from the melon plants of the invention, where optionally, the regenerable cells are: (a) embryos, meristem, leaves, pollen, cotyledons, hypocotyls, roots, root tips, anthers, flowers, pistils, ovules, seed, shoots, stems, stalks, petioles, pith and/or capsules; or (b) callus or protoplasts derived from the cells of (a). Further provided are melon plants regenerated from a tissue culture of the invention.

These and other aspects of the present invention are set forth in the detailed description of the invention below.

DETAILED DESCRIPTION OF THE INVENTION

The present invention is based, in part, on the development of novel melon cultivars having desirable properties including non-climacteric fruit ripening and/or producing a fruit with a firm flesh and/or high soluble solids. In representative embodiments, the melon plants of the invention produce fruit have a higher sugar (e.g., sucrose) content and/or having a sweeter taste. The melon plants of the invention may advantageously having a longer field shelf life and/or longer post-harvest shelf life and/or be more suitable for long-distance shipping.

It should be appreciated that the invention can be embodied in different forms and should not be construed as limited to the embodiments set forth herein. Rather, these embodiments are provided so that this disclosure will be thorough and complete, and will fully convey the scope of the invention to those skilled in the art.

Unless otherwise defined, all technical and scientific terms used herein have the same meaning as commonly understood by one of ordinary skill in the art to which this invention belongs. The terminology used in the description of the invention herein is for the purpose of describing particular embodiments only and is not intended to be limiting of the invention.

Unless the context indicates otherwise, it is specifically intended that the various features and embodiments of the invention described herein can be used in any combination.

Moreover, the present invention also contemplates that in some embodiments of the invention, any feature or combination of features set forth herein can be excluded or omitted. To illustrate, if the specification states that a composition comprises components A, B and C, it is specifically intended that any of A, B or C, or a combination thereof, can be omitted and disclaimed singularly or in any combination.

Unless otherwise defined, all technical and scientific terms used herein have the same meaning as commonly understood by one of ordinary skill in the art to which this invention belongs. The terminology used in the description of the invention herein is for the purpose of describing particular embodiments only and is not intended to be limiting of the invention.

All publications, patent applications, patents, and other references mentioned herein are incorporated by reference in their entirety.

I. DEFINITIONS

In the description and tables which follow, a number of terms are used. In order to provide a clear and consistent understanding of the specification and claims, including the scope to be given such terms, the following definitions are provided:

As used in the description of the invention and the appended claims, the singular forms "a," "an" and "the" are intended to include the plural forms as well, unless the context clearly indicates otherwise.

As used herein, "and/or" refers to and encompasses any and all possible combinations of one or more of the associated listed items, as well as the lack of combinations when interpreted in the alternative ("or").

The term "about," as used herein when referring to a measurable value such as a dosage or time period and the like, is meant to encompass variations of ±20%, ±10%, ±5%, ±1%, ±0.5%, or even ±0.1% of the specified amount.

The term "comprise," "comprises" and "comprising" as used herein, specify the presence of the stated features, integers, steps, operations, elements, and/or components, but do not preclude the presence or addition of one or more other features, integers, steps, operations, elements, components, and/or groups thereof.

As used herein, the transitional phrase "consisting essentially of" means that the scope of a claim is to be interpreted to encompass the specified materials or steps recited in the claim "and those that do not materially affect the basic and novel characteristic(s)" of the claimed invention. See, *In re Herz*, 537 F.2d 549, 551-52, 190 U.S.P.Q. 461, 463 (CCPA 1976) (emphasis in the original); see also MPEP §2111.03. Thus, the term "consisting essentially of" when used in a claim or the description of this invention is not intended to be interpreted to be equivalent to "comprising."

"Allele". An allele is any of one or more alternative forms of a gene, all of which relate to a trait or characteristic. In a diploid cell or organism, the two alleles of a given gene occupy corresponding loci on a pair of homologous chromosomes.

"Backcrossing". Backcrossing is a process in which a breeder repeatedly crosses hybrid progeny back to one of the parents, for example, a first generation hybrid $F_1$ with one of the parental genotype of the $F_1$ hybrid.

"Cotyledon". One of the first leaves of the embryo of a seed plant; typically one or more in monocotyledons, two in dicotyledons, and two or more in gymnosperms.

"Gene". As used herein, "gene" refers to a segment of nucleic acid comprising an open reading frame. A gene can be introduced into a genome of a species, whether from a different species or from the same species, using transformation or various breeding methods.

"Plant." As used herein, the term "plant" includes plant cells, plant protoplasts, plant cell tissue cultures from which plants can be regenerated, plant calli, plant clumps, and plant cells that are intact in plants or parts of plants, such as leaves, pollen, embryos, cotyledons, hypocotyl, roots, root tips, anthers, pistils, flowers, ovules, seeds, fruit, stems, and the like.

"Plant material". The terms "plant material" and "material obtainable from a plant" are used interchangeably herein and refer to any plant material obtainable from a plant including without limitation, leaves, stems, roots, flowers or flower parts, fruits, pollen, egg cells, zygotes, seeds, cuttings, cell or tissue cultures, or any other part or product of the plant.

"Plant part". As used herein, a "plant part" includes any part, organ, tissue or cell of a plant including without limitation an embryo, meristem, leaf, pollen, cotyledon, hypocotyl, root, root tip, anther, flower, flower bud, pistil, ovule, seed, shoot, stem, stalk, petiole, pith, capsule, a scion, a rootstock and/or a fruit including callus and protoplasts derived from any of the foregoing.

"Quantitative Trait Loci". Quantitative Trait Loci (QTL) refers to genetic loci that control to some degree, numerically representable traits that are usually continuously distributed.

"Regeneration". Regeneration refers to the development of a plant from tissue culture.

"Resistance". As used herein the terms "resistance" and "tolerance" (and grammatical variations thereof) are used interchangeably to describe plants that show reduced or essentially no symptoms to a specific biotic (e.g., a pest, pathogen or disease) or abiotic (e.g., exogenous or environmental, including herbicides) factor or stressor. In some embodiments, "resistant" or "tolerant" plants show some symptoms but are still able to produce marketable product with an acceptable yield, e.g., the yield may still be reduced and/or the plants may be stunted as compared with the yield or growth in the absence of the biotic and/or abiotic factor or stressor. Those skilled in the art will appreciate that the degree of resistance or tolerance may be assessed with respect to a plurality or even an entire field of plants. A melon plant may be considered "resistant" or "tolerant" if resistance/tolerance is observed over a plurality of plants (e.g., an average), even if particular individual plants may be susceptible to the biotic or abiotic factor or stressor.

"RHS". RHS refers to the Royal Horticultural Society of England which publishes an official botanical color chart quantitatively identifying colors according to a defined numbering system. The chart may be purchased from Royal Horticulture Society Enterprise Ltd., RHS Garden; Wisley, Woking; Surrey GU236QB, UK.

"Single gene converted". A single gene converted or conversion plant refers to a plant that is developed by a plant breeding technique called backcrossing or via genetic engineering wherein essentially all of the desired morphological and physiological characteristics of a line are recovered in addition to the single gene transferred into the line via the backcrossing technique or via genetic engineering.

"Substantially equivalent characteristic". A characteristic that, when compared, does not show a statistically significant difference (e.g., p=0.05) from the mean.

"Transgene". A nucleic acid of interest that can be introduced into the genome of a plant by genetic engineering techniques (e.g., transformation) or breeding. The transgene can be from the same or a different species. If from the same species, the transgene can be an additional copy of a native coding sequence or can present the native sequence in a form or context (e.g., different genomic location and/or in operable association with exogenous regulatory elements such as a promoter) than is found in the native state. The transgene can encode a polypeptide or a functional non-translated RNA (e.g., RNAi).

Botanical Description of the Novel Melon Plants of the Invention.

In representative embodiments, the melon plants of the invention have non-climacteric fruit ripening. Climacteric ripening is characterized by an upsurge in the respiration rate accompanying the autocatalytic ethylene production peak during fruit ripening (Kays, S. J., Paull, R. E., 2004. Metabolic processes in harvested products. In: Postharvest Biology. Exon Press, Athens, Ga., pp. 79-136). Due to climacteric fruit ripening, there is abscission layer formation at the peduncle attachment of the fruit. Commercially, fruit that exhibit climacteric behavior have a shorter shelf-life and higher aroma levels than non-climacteric fruit. In contrast, non-climacteric fruit ripening involves less cyanide-insensitive respiration as compared with climacteric fruit, and the upsurge in respiration and ethylene is not observed or is transitory after ethylene application in non-climacteric fruit, and there is no abscission layer formation (Id.). In general, non-climacteric melon types show lower levels of total aromatic compounds (Moshonas, M. G., Shaw, P. E., Baldwin, E. A., Yuen, W., 1993. Volatile and nonvolatile components in Hami melon (*Cucumis melo* L.). Lebensm. Wiss. Technol. 26, 577-589) because some aromatic compounds are produced only by ethylene-dependent pathways. In addition, fruit with non-climacteric fruit ripening generally has a longer field shelf life and post-harvest shelf life.

In representative embodiments, the melons of the invention produce a mature fruit having a firm flesh (e.g., a firmer flesh than a western shipper cantaloupe such as Gold Express). For example, in embodiments, the melon plants produce a fruit having at maturity a flesh firmness of at least about 4.25, 4.5, 4.75, 5, 5.25, 5.5, 5.75 or 6 pound force (e.g., when measured with a FT011 penetrometer with an 8 mm probe size). One exemplary method for measuring flesh firmness is to insert the tip of a penetrometer into the flesh of the melon up to about 0.5 inches deep. Multiple measurements at different sites (e.g., three measurements/sites) in the fruit can be made to determine an average flesh firmness. In general, a traditional western shipper cantaloupe has a mature flesh firmness of about 4 pound force.

In other embodiments, the melons of the invention produce a mature fruit have a relatively high total soluble solids (e.g., as compared with a conventional western shipper cantaloupe such as Gold Express). In exemplary embodiments, the melons of the invention produce a mature fruit having total soluble solids of at least about 12.1° Brix, 12.2° Brix, 12.3° Brix, 12.4° Brix, 12.5° Brix, 12.75° Brix, 13° Brix, 13.25° Brix, 13.5° Brix, 13.75° Brix or 14° Brix. Typically, a western shipper cantaloupe has a total soluble solids value of about 10-12° Brix.

Optionally, the melon plants of the invention have a relatively high carbohydrate content (e.g., sucrose) and/or a higher sweetness index (e.g., as compared with a conventional western shipper cantaloupe such as Gold Express). In representative embodiments, the melon plants produce a fruit having at maturity a sucrose content of at least about 2.6%, 2.65%, 2.7%, 2.75%, 2.8%. 2.85%, 2.9%, 2.95% or 3% (as a percentage of total soluble solids). In representative embodiments, the melon plants produce a fruit having at maturity a fructose content of at least about 2.5%, 2.55%, 2.6%, 2.65%, 2.7% or 2.75% (as a percentage of total soluble solids).

Those skilled in the art will appreciate that cantaloupe plants can be readily crossed with other melons, e.g., another *C. melo* melon including without limitation, honeydew, Tuscan, Piel de Sapo, Yellow Canary, Japanese, Charentais, Galia, Amarello, Kirkagak, Hamy, Ananas, Oriental, and the like. Thus, the melon plants of the invention encompass hybrid melon plants arising from crosses between cantaloupe cultivar ME007 or ME009 and another melon plant (cantaloupe or other melon), as well as melon plants derived from cantaloupe cultivar ME007 or ME009 that have a lineage including any of cantaloupe cultivar ME007 and ME009 and another melon plant (cantaloupe or other melon type).

Botanical descriptions of cantaloupe varieties ME007 or ME009 are provided below.

ME007

Breeding methods. Melon line ME007 was developed using the modified pedigree method of breeding. Line ME007 was stable for phenotypic traits such as fruit size and shape, uniformity, flesh firmness, and total soluble solids (e.g., no variations or off-types).

Hybrid production. Test crosses have been made with ME007 at F7 as the female parent, and a number of promising hybrids have been identified (e.g., ME012 and ME014; U.S. Pat. No. 8,618,361).

Morphological and physiological characteristics of ME007. To the best of the inventors' knowledge, ME007 is most similar to Gold Express.

As compared with the variety Gold Express, ME007 has non-climacteric fruit ripening (i.e., no abscission layer formation). Due to non-climacteric fruit ripening in ME007, there is no increase in respiration rate; hence, the fruit does not abscise from the vine and stays on the vine longer. This characteristic enables the melons to be harvested in fewer periods as compared with a climacteric melon (e.g., about 2-3 as compared with 12-14), which will abscise from the vine and need to be harvested more frequently. In addition, ME007 has a high total soluble solids and a firm flesh as compared with traditional western shipper cantaloupe. ME007 has a soluble solids of at least about 14° Brix and flesh firmness of at least about 6 pound force. Normally, traditional western shippers have total soluble solids of about 10-12° Brix and a flesh firmness of about 4 pound force.

As far as the inventors are aware, these three traits (non-climacteric fruit ripening, high total solids and flesh firmness) have not previously been combined in a single line.

ME007 is best adapted to the Southern and Southwestern regions of the United States. ME007 produces a round fruit with a conspicuous blossom scar.

Figure 1:
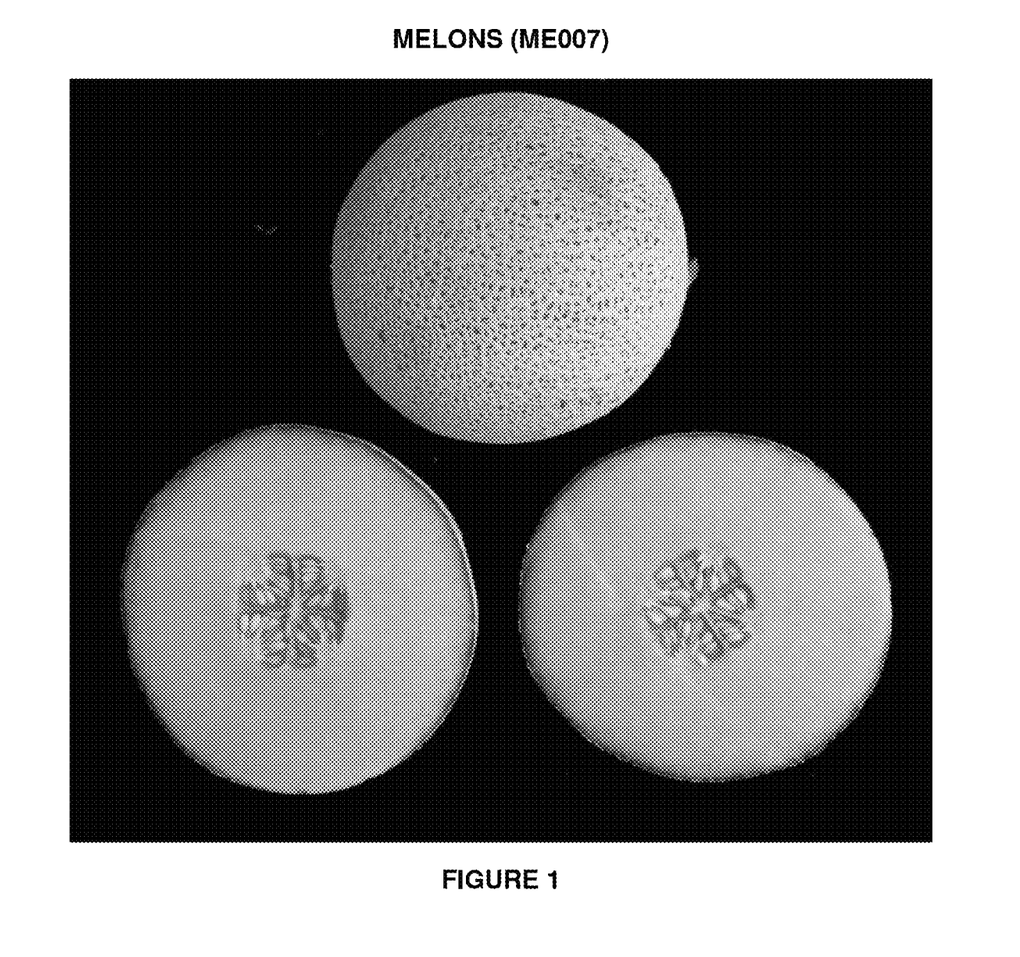
FIG. 1 is a photograph showing the exterior and interior of the fruit of melon cultivar ME007.

A photograph showing the exterior and interior of fruit from melon cultivar ME007 is shown as FIG. 1.

Further description of ME007 and comparison with Gold Express are provided in Table 1.

TABLE 1

Morphological and Physiological Characteristics of ME007 as compared with Gold Express.

| Descriptor | ME007 | Gold Express |
|---|---|---|
| Area of best adaptation in U.S. | Most areas | Southwest |
| Maturity (days from seeding to harvest) | 75 | 69 |
| Plant: | | |
| Fertility | Andromonoecious | Andromonoecious |
| Habit | Vine | Vine |
| Leaf (mature blade of third leaf): | | |
| Shape | Reniform | Reniform |
| Lobes | Not lobed | Shallowly lobed |
| Color | Dark green (RHS 137A) | Dark Green (RHS 137A) |
| Length (mm) | 103 | 106 |
| Width (mm) | 142 | 147 |
| Surface | Pubescent | Pubescent |
| Fruit (at edible maturity): | | |
| Length (cm) | 16.9 | 15 |
| Diameter (cm) | 16 | 14 |
| Weight (gm) | 2276 | 1560 |
| Shape | Round | Oval |
| Surface | Netted | Netted |
| Blossom scar | Conspicuous | Conspicuous |
| Rib presence | Absent | Absent |
| Shipping quality | Excellent (long distance shipping) | Fair (short distance shipping) |
| Fruit abscission | Does not abscise | When ripe |
| Rind net: | | |
| Net presence | Abundant | Abundant |
| Distribution | Covers entire fruit | Covers entire fruit |
| Coarseness | Medium coarse | Very coarse |
| Interlacing | Complete | Complete |
| Interstices | Medium deep | Deep |
| Rind texture: | | |
| Texture | Hard | Firm |
| Thickness at medial (mm) | 6 | 15 |
| Rind color at edible maturity: | | |
| Primary color | Green (RHS 136B) | Green (RHS 133A) |
| Net color | Brown (RHS 161C) | Brown (RHS 199D) |
| Rind color at edible maturity: | | |
| Primary color | Green (RHS 136B) | Yellow (RHS 20A) |
| Net color | Brown (RHS 161C) | Brown (RHS 199D) |
| Flesh at edible maturity: | | |
| Color near cavity | Orange (RHS 26B) | Orange (RHS 25B) |
| Color in center | Orange (RHS 26B) | Orange (RHS 25B) |
| Color near rind | Green (RHS 140C) | Green (RHS 143A) |
| Refractometer % soluble solids (center of flesh) | 12 | 12 |
| Aroma | Faint | Faint |
| Flavor | Mild | Mild |
| Seed cavity: | | |
| Length (mm) | 53 | 63 |
| Width (mm) | 53 | 60 |
| Shape in X-section | Circular | Triangular |
| Seeds: | | |
| No. seeds per fruit | 535 | 556 |
| Grams per 1000 seeds | 27.9 | 27 |

TABLE 1-continued

Morphological and Physiological Characteristics of ME007 as compared with Gold Express.

| Descriptor | ME007 | Gold Express |
|---|---|---|
| Disease resistance: | | |
| Powdery mildew | Not tested | Resistant |
| Sulphur burn | Resistant | Resistant |
| *Fusarium* wilt | Resistant | Resistant |
| Melon necrotic spot virus | Resistant | Not tested |

Disease resistance. In addition to what is described above, ME007 is resistant to *Fusarium* wilt race 1 and 2. The disease test results and marker profile for ME007 against *Fusarium* wilt race 1 and 2 are shown below in Table 2. A standard root dip method was used for inoculation of *Fusarium* wilt races 1 and 2. In addition to the standard disease test, resistance was also determined using marker assisted trait selection (Tezuka et al., 2011, Plant Breeding 130: 261-267; Risser et al., 1973, Ann. Amélior Plantes 23:259-263).

TABLE 2

Disease screen for resistance to Fusarium wilt race 1 and Fusarium wilt race 2 in ME007.

| | Fusarium race 2 | | | Fusarium race 1 | | |
|---|---|---|---|---|---|---|
| Variety | # plants tested | Resistant | Susceptible | # plants tested | Resistant | Susceptible |
| ME007 | 60 | 60 | 0 | 60 | 60 | 0 |
| A055 (resistant control) | 60 | 60 | 0 | 60 | 60 | 0 |
| Tam Uvalde (susceptible control) | 60 | 0 | 60 | 60 | 0 | 60 |

ME009

Breeding methods. Melon line ME009 was developed using the modified pedigree method of breeding. Line ME009 was stable for phenotypic traits such as fruit size and shape, uniformity, flesh firmness, and total soluble solids (e.g., no variations or off-types).

Hybrid production. Test crosses have been made with ME009 at F7 as the female parent, and a number of promising hybrids have been identified (e.g., ME011; U.S. Pat. No. 8,618,361).

Morphological and physiological characteristics of ME009. To the best of the inventors' knowledge, ME009 is most similar to Gold Express.

As compared with the variety Gold Express, ME009 has non-climacteric fruit ripening (i.e., no abscission layer formation). Due to non-climacteric fruit ripening in ME009, there is no increase in respiration rate; hence, the fruit does not abscise from the vine and stays on the vine longer. This characteristic enables the melons to be harvested in fewer periods as compared with a climacteric melon (e.g., about 2-3 as compared with 12-14), which will abscise from the vine and need to be harvested more frequently. In addition, ME009 has a high total soluble solids and a firm flesh as compared with traditional western shipper cantaloupe. ME009 has a high soluble solids of at least about 14° Brix and flesh firmness of at least about 6 pound force. Normally, traditional western shippers have total soluble solids of about 10-12° Brix and a flesh firmness of about 4 pound force.

As far as the inventors are aware, these three traits (non-climacteric fruit ripening, high total solids and flesh firmness) have not previously been combined in a single line.

ME009 is best adapted to the Southern and Southwestern regions of the United States. ME009 produces a round fruit with a conspicuous blossom scar.

Figure 2:
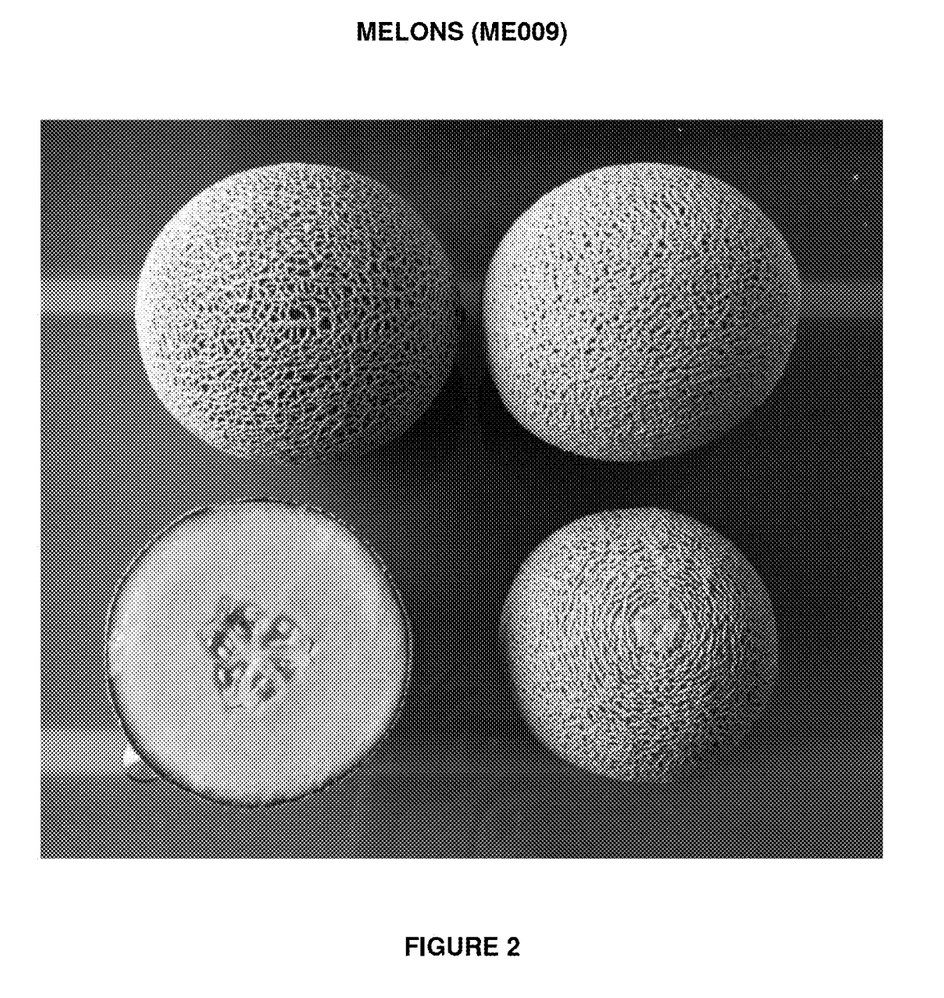
FIG. 2 is a photograph showing the exterior and interior of the fruit of melon cultivar ME009.

A photograph showing the exterior and interior of fruit from melon cultivar ME009 is shown as FIG. 2.

Further description of ME009 and comparison with Gold Express are provided in Table 3.

TABLE 3

Morphological and Physiological Characteristics of ME009 as compared with Gold Express.

| Descriptor | ME009 | Gold Express |
|---|---|---|
| Area of best adaptation in U.S. | Most areas | Southwest |
| Maturity (days from seeding to harvest) | 75 | 69 |
| Plant: | | |
| Fertility | Andromonoecious | Andromonoecious |
| Habit | Vine | Vine |
| Leaf (mature blade of third leaf): | | |
| Shape | Reniform | Reniform |
| Lobes | Not lobed | Shallowly lobed |
| Color | Dark green (RHS 137A) | Dark Green (RHS 137A) |
| Length (mm) | 103 | 106 |
| Width (mm) | 142 | 147 |
| Surface | Pubescent | Pubescent |
| Fruit (at edible maturity): | | |
| Length (cm) | 14.9 | 15 |
| Diameter (cm) | 15.5 | 14 |
| Weight (gm) | 1780 | 1560 |
| Shape | Round | Oval |
| Surface | Netted | Netted |
| Blossom scar | Conspicuous | Conspicuous |
| Rib presence | Absent | Absent |
| Shipping quality | Excellent (long distance shipping) | Fair (short distance shipping) |
| Fruit abscission | Does not abscise | When ripe |
| Rind net: | | |
| Net presence | Abundant | Abundant |
| Distribution | Covers entire fruit | Covers entire fruit |
| Coarseness | Medium coarse | Very coarse |
| Interlacing | Complete | Complete |
| Interstices | Medium deep | Deep |
| Rind texture: | | |
| Texture | Hard | Firm |
| Thickness at medial (mm) | 6 | 15 |
| Rind color at edible maturity: | | |
| Primary color | Green (RHS 136B) | Green (RHS 133A) |
| Net color | Brown (RHS 161C) | Brown (RHS 199D) |
| Rind color at edible maturity: | | |
| Primary color | Green (RHS 136B) | Yellow (RHS 20A) |
| Net color | Brown (RHS 161C) | Brown (RHS 199D) |
| Flesh at edible maturity: | | |
| Color near cavity | Orange (RHS 26B) | Orange (RHS 25B) |
| Color in center | Orange (RHS 26B) | Orange (RHS 25B) |
| Color near rind | Green (RHS 140C) | Green (RHS 143A) |
| Refractometer % soluble solids (center of flesh) | 12 | 12 |
| Aroma | Faint | Faint |
| Flavor | Mild | Mild |

TABLE 3-continued

Morphological and Physiological Characteristics of ME009 as compared with Gold Express.

| Descriptor | ME009 | Gold Express |
| --- | --- | --- |
| Seed cavity: | | |
| Length (mm) | 53 | 63 |
| Width (mm) | 53 | 60 |
| Shape in X-section | Circular | Triangular |
| Seeds: | | |
| No. seeds per fruit | 535 | 556 |
| Grams per 1000 seeds | 27.9 | 27 |
| Disease resistance: | | |
| Powdery mildew | Resistant | Resistant |
| Sulphur burn | Resistant | Resistant |
| *Fusarium* wilt | Resistant | Resistant |
| Melon necrotic spot virus | Resistant | Not tested |

Disease resistance. In addition to what is described above, ME009 is resistant to *Fusarium* wilt race 1, *Fusarium* race 2 and powdery mildew race 2. The disease test results and marker profile for ME009 against *Fusarium* wilt race 1 and 2 are shown below in Table 4. A standard root dip method was used for inoculation of *Fusarium* wilt races 1 and 2. In addition to the standard disease test, resistance was also determined using marker assisted trait selection (Tezuka et al., 2011, Plant Breeding 130: 261-267; Risser et al., 1973, Ann. Amélior Plantes 23:259-263). Resistance to powdery mildew race 2 (results shown in Table 5), was tested as described previously (McCrieght, 2006, J. Amer. Soc. Hort. Sci. 131: 59-65).

TABLE 4

Disease screen for resistance to Fusarium wilt race 1 and Fusarium wilt race 2 in ME009.

| | Fusarium race 2 | | | Fusarium race 1 | | |
| --- | --- | --- | --- | --- | --- | --- |
| Variety | #plants tested | Resistant | Susceptible | #plants tested | Resistant | Susceptible |
| ME009 | 60 | 60 | 0 | 60 | 60 | 0 |
| A055 (resistant control) | 60 | 60 | 0 | 60 | 60 | 0 |
| Tam Uvalde (susceptible control) | 60 | 0 | 60 | 60 | 0 | 60 |

TABLE 5

Disease screen for resistance to powdery mildew race 1 and powdery mildew race 2 US in ME009.

| | Powdery mildew race 1 test | | | Powdery mildew race 2 US test | | |
| --- | --- | --- | --- | --- | --- | --- |
| Variety | # plants tested | Resistant | Susceptible | # plants tested | Resistant | Susceptible |
| ME009 | 60 | 60 | 0 | 60 | 60 | 0 |
| Tam Uvalde (resistant control) | 60 | 60 | 0 | 60 | 60 | 0 |
| A045 (susceptible control) | 60 | 0 | 60 | 60 | 0 | 60 |

Further Embodiments of the Invention

With the advent of molecular biological techniques that have allowed the isolation and characterization of genes that encode specific protein products, scientists in the field of plant biology developed a strong interest in engineering the genome of plants to contain and express foreign nucleic acids, or additional, or modified versions of native, or endogenous, nucleic acids (e.g., driven by different promoters) in order to alter the traits of a plant in a specific manner. Any DNA sequences, whether from a different species or from the same species, which are introduced into the genome using transformation or various breeding methods, are referred to herein collectively as "transgenes." Over the last fifteen to twenty years, several methods for producing transgenic plants have been developed, and the present invention, in particular embodiments, also relates to transformed versions of melon plants disclosed herein.

Plant transformation generally involves the construction of an expression vector that will function in plant cells. Optionally, such a vector comprises one or more nucleic acids comprising a coding sequence for a polypeptide or an untranslated functional RNA under control of, or operatively linked to, a regulatory element (for example, a promoter). In representative embodiments, the vector(s) may be in the form of a plasmid, and can be used alone or in combination with other plasmids, to provide transformed melon plants using transformation methods as described herein to incorporate transgenes into the genetic material of the melon plant.

Additional methods include, but are not limited to, expression vectors introduced into plant tissues using a direct nucleic acid transfer method, such as microprojectile-mediated delivery (e.g., with a biolistic device), DNA injection, *Agrobacterium*-mediated transformation, electroporation, and the like. Transformed plants obtained from the plants (and parts and tissue culture thereof) of the invention are intended to be within the scope of this invention.

Expression Vectors for Plant Transformation—Selectable Markers.

Expression vectors typically include at least one nucleic acid comprising or encoding a selectable marker, operably linked to a regulatory element (for example, a promoter) that allows transformed cells containing the marker to be either recovered by negative selection, e.g., inhibiting growth of cells that do not contain the selectable marker, or by positive selection, e.g., screening for the product encoded by the selectable marker. Many commonly used selectable markers for plant transformation are well known in the transformation art, and include, for example, nucleic acids that code for enzymes that metabolically detoxify a selective chemical agent which may be an antibiotic or an herbicide, or nucleic acids that encode an altered target which is insensitive to the inhibitor. Positive selection methods are also known in the art.

One commonly used selectable marker for plant transformation is a neomycin phosphotransferase II (nptII) coding sequence, for example, isolated from transposon Tn5, which when placed under the control of plant regulatory signals confers resistance to kanamycin. Fraley, et al., PNAS, 80:4803 (1983). Another commonly used selectable marker is hygromycin phosphotransferase, which confers resistance to the antibiotic hygromycin. Vanden Elzen, et al., Plant Mol. Biol., 5:299 (1985).

Additional selectable markers of bacterial origin that confer resistance to antibiotics include gentamycin acetyl transferase, streptomycin phosphotransferase, aminoglycoside-3'-adenyl transferase, the bleomycin resistance determinant. Hayford, et al., Plant Physiol., 86:1216 (1988); Jones, et al., Mol. Gen. Genet., 210:86 (1987); Svab, et al., Plant Mol. Biol., 14:197 (1990); Hille, et al., Plant Mol. Biol., 7:171 (1986). Other selectable markers confer resistance to herbicides such as glyphosate, glufosinate, or bromoxynil. Comai, et al., Nature, 317:741-744 (1985); Gordon-Kamm, et al., Plant Cell, 2:603-618 (1990); and Stalker, et al., Science, 242:419-423 (1988).

Selectable markers for plant transformation that are not of bacterial origin include, for example, mouse dihydrofolate reductase, plant 5-enolpyruvylshikimate-3-phosphate synthase, and plant acetolactate synthase. Eichholtz, et al., Somatic Cell Mol. Genet., 13:67 (1987); Shah, et al., Science, 233:478 (1986); and Charest, et al., Plant Cell Rep., 8:643 (1990).

Another class of selectable marker for plant transformation involves screening of presumptively transformed plant cells rather than direct genetic selection of transformed cells for resistance to a toxic substance such as an antibiotic. These selectable markers are particularly useful to quantify or visualize the spatial pattern of expression of a transgene in specific tissues and are frequently referred to as a reporter gene because they can be fused to transgene or regulatory sequence for the investigation of nucleic acid expression. Commonly used reporters for screening presumptively transformed cells include alpha-glucuronidase (GUS), alpha-galactosidase, luciferase and chloramphenicol, acetyltransferase. Jefferson, R. A., Plant Mol. Biol., 5:387 (1987); Teeri, et al., EMBO J., 8:343 (1989); Koncz, et al., PNAS, 84:131 (1987); and DeBlock, et al., EMBO J., 3:1681 (1984).

In vivo methods for visualizing GUS activity that do not require destruction of plant tissues are available. Molecular Probes, Publication 2908, IMAGENE GREEN, pp. 1-4 (1993) and Naleway, et al., J. Cell Biol., 115:151 a (1991).

Green Fluorescent Protein (GFP) is also utilized as a marker for nucleic acid expression in prokaryotic and eukaryotic cells. Chalfie, et al., Science, 263:802 (1994). GFP and mutants of GFP may be used as screenable markers.

Expression Vectors for Plant Transformation—Promoters.

Transgenes included in expression vectors are generally driven by a nucleotide sequence comprising a regulatory element (for example, a promoter). Numerous types of promoters are well known in the transformation arts, as are other regulatory elements that can be used alone or in combination with promoters.

As used herein, "promoter" includes reference to a region of DNA upstream from the start of transcription and involved in recognition and binding of RNA polymerase and other proteins to initiate transcription. A "plant promoter" is a promoter capable of initiating transcription in plant cells.

Examples of promoters under developmental control include promoters that preferentially initiate transcription in certain tissues, such as leaves, roots, seeds, fibers, xylem vessels, tracheids, or sclerenchyma. Such promoters are referred to as "tissue-preferred." Promoters that initiate transcription only in certain tissue are referred to as "tissue-specific." A "cell type" specific promoter preferentially drives expression in certain cell types in one or more organs, for example, vascular cells in roots or leaves. An "inducible" promoter is a promoter that is under environmental control. Examples of environmental conditions that may affect transcription by inducible promoters include anaerobic conditions or the presence of light. Tissue-specific, tissue-preferred, cell type specific, and inducible promoters constitute the class of "non-constitutive" promoters. A "constitutive" promoter is a promoter that is active under most environmental conditions.

A. Inducible Promoters:

An inducible promoter is operably linked to a nucleic acid for expression in a plant. Optionally, the inducible promoter is operably linked to a nucleotide sequence encoding a signal sequence which is operably linked to a nucleic acid for expression in the plant. With an inducible promoter, the rate of transcription increases in response to an inducing agent.

Any inducible promoter can be used in the instant invention. See Ward, et al., Plant Mol. Biol., 22:361-366 (1993). Exemplary inducible promoters include, but are not limited to, that from the ACEI system which responds to copper (Melt, et al., PNAS, 90:4567-4571 (1993)); promoter from the In2 gene from maize which responds to benzenesulfonamide herbicide safeners (Hershey, et al., Mol. Gen. Genet., 227:229-237 (1991) and Gatz, et al., Mol. Gen. Genet., 243: 32-38 (1994)) or Tet repressor from Tn10 (Gatz, et al., Mol. Gen. Genet., 227:229-237 (1991)). A representative inducible promoter is a promoter that responds to an inducing agent to which plants do not normally respond. An exemplary inducible promoter is the inducible promoter from a steroid hormone gene, the transcriptional activity of which is induced by a glucocorticosteroid hormone. Schena, et al., PNAS, 88:0421 (1991).

B. Constitutive Promoters:

A constitutive promoter is operably linked to a nucleic acid for expression in a plant or the constitutive promoter is operably linked to a nucleotide sequence encoding a signal sequence which is operably linked to a nucleic acid for expression in a plant.

Many different constitutive promoters can be utilized in the instant invention. Exemplary constitutive promoters include, but are not limited to, the promoters from plant viruses such as the 35S promoter from CaMV (Odell, et al., Nature, 313:810-812 (1985)) and the promoters from such genes as rice actin (McElroy, et al., Plant Cell, 2:163-171 (1990)); ubiquitin (Christensen, et al., Plant Mol. Biol., 12:619-632 (1989) and Christensen, et al., Plant Mol. Biol., 18:675-689 (1992)); pEMU (Last, et al., Theor. Appl. Genet., 81:581-588 (1991)); MAS (Velten, et al., EMBO J., 3:2723-2730 (1984)) and maize H3 histone (Lepetit, et al., Mol. Gen. Genet., 231:276-285 (1992) and Atanassova, et al., Plant J., 2 (3):291-300 (1992)). The ALS promoter, XbaI/NcoI fragment 5' to the *Brassica napus* ALS3 structural gene (or a nucleotide sequence similarity to said XbaI/NcoI fragment), represents a particularly useful constitutive promoter. See PCT Application No. WO 96/30530.

C. Tissue-Specific or Tissue-Preferred Promoters:

A tissue-specific promoter is operably linked to a nucleic acid for expression in a plant. Optionally, the tissue-specific promoter is operably linked to a nucleotide sequence encoding a signal sequence which is operably linked to a nucleic acid for expression in a plant. Plants transformed with a nucleic acid of interest operably linked to a tissue-specific promoter transcribe the nucleic acid of interest exclusively, or preferentially, in a specific tissue.

Any tissue-specific or tissue-preferred promoter can be utilized in the instant invention. Exemplary tissue-specific or tissue-preferred promoters include, but are not limited to, a root-preferred promoter, such as that from the phaseolin gene (Murai, et al., Science, 23:476-482 (1983) and Sengupta-Gopalan, et al., PNAS, 82:3320-3324 (1985)); a leaf-specific and light-induced promoter such as that from cab or rubisco (Simpson, et al., EMBO J., 4(11):2723-2729 (1985) and Timko, et al., Nature, 318:579-582 (1985)); an anther-specific promoter such as that from LAT52 (Twell, et al., Mol. Gen. Genet., 217:240-245 (1989)); a pollen-specific promoter such as that from Zm13 (Guerrero, et al., Mol. Gen.

Genet., 244:161-168 (1993)) or a microspore-preferred promoter such as that from apg (Twell, et al., Sex. Plant Reprod., 6:217-224 (1993)).

Signal Sequences for Targeting Proteins to Subcellular Compartments.

Transport of polypeptides produced by transgenes to a subcellular compartment such as the chloroplast, vacuole, peroxisome, glyoxysome, cell wall, or mitochondrion, or for secretion into the apoplast, is generally accomplished by means of operably linking a nucleotide sequence encoding a signal sequence to the 5' and/or 3' region of a nucleic acid encoding the polypeptide of interest. Signal sequences at the 5' and/or 3' end of the coding sequence target the polypeptide to particular subcellular compartments.

The presence of a signal sequence can direct a polypeptide to either an intracellular organelle or subcellular compartment or for secretion to the apoplast. Many signal sequences are known in the art. See, for example, Becker, et al., Plant Mol. Biol., 20:49 (1992); Close, P. S., Master's Thesis, Iowa State University (1993); Knox, C., et al., "Structure and Organization of Two Divergent Alpha-Amylase Genes from Barley," Plant Mol. Biol., 9:3-17 (1987); Lerner, et al., Plant Physiol., 91:124-129 (1989); Fontes, et al., Plant Cell, 3:483-496 (1991); Matsuoka, et al., PNAS, 88:834 (1991); Gould, et al., J. Cell. Biol., 108:1657 (1989); Creissen, et al., Plant J, 2:129 (1991); Kalderon, et al., A short amino acid sequence able to specify nuclear location, Cell, 39:499-509 (1984); and Steifel, et al., Expression of a maize cell wall hydroxyproline-rich glycoprotein gene in early leaf and root vascular differentiation, Plant Cell, 2:785-793 (1990).

Foreign Polypeptide Transgenes and Agronomic Transgenes.

With transgenic plants according to the present invention, a foreign protein can be produced in commercial quantities. Thus, techniques for the selection and propagation of transformed plants, which are well understood in the art, yield a plurality of transgenic plants which are harvested in a conventional manner, and a foreign polypeptide then can be extracted from a tissue of interest or from total biomass. Protein extraction from plant biomass can be accomplished by known methods which are discussed, for example, by Heney and Orr, Anal. Biochem., 114:92-6 (1981).

According to a representative embodiment, the transgenic plant provided for commercial production of foreign protein is a melon plant of the invention. In another embodiment, the biomass of interest is seed. For the relatively small number of transgenic plants that show higher levels of expression, a genetic map can be generated, for example via conventional RFLP, PCR, and SSR analysis, which identifies the approximate chromosomal location of the integrated DNA molecule. For exemplary methodologies in this regard, see Methods in Plant Molecular Biology and Biotechnology, Glick and Thompson Eds., 269:284, CRC Press, Boca Raton (1993). Map information concerning chromosomal location is useful for proprietary protection of a subject transgenic plant. If unauthorized propagation is undertaken and crosses made with other germplasm, the map of the integration region can be compared to similar maps for suspect plants, to determine if the latter have a common parentage with the subject plant. Map comparisons can involve hybridizations, RFLP, PCR, SSR, and sequencing, all of which are conventional techniques.

Likewise, by means of the present invention, agronomic transgenes can be expressed in transformed plants. More particularly, plants can be genetically engineered to express various phenotypes of agronomic interest. Exemplary nucleic acids of interest in this regard include, but are not limited to, those categorized below:

A. Transgenes that Confer Resistance to Pests or Disease:

1. Plant disease resistance transgenes. Plant defenses are often activated by specific interaction between the product of a disease resistance gene (R) in the plant and the product of a corresponding avirulence (Avr) gene in the pathogen. A plant line can be transformed with a cloned resistance transgene to engineer plants that are resistant to specific pathogen strains. See, for example, Jones, et al., Science, 266:789 (1994) (cloning of the tomato Cf-9 gene for resistance to *Cladosporium fulvum*); Martin, et al., Science, 262:1432 (1993) (tomato Pto gene for resistance to *Pseudomonas syringae* pv. tomato encodes a protein kinase); and Mindrinos, et al., Cell, 78:1089 (1994) (Arabidopsis RSP2 gene for resistance to *Pseudomonas syringae*).

2. A *Bacillus thuringiensis* protein, a derivative thereof, or a synthetic polypeptide modeled thereon. See, for example, Geiser, et al., Gene, 48:109 (1986), who disclose the cloning and nucleotide sequence of a Bt delta-endotoxin gene. Moreover, DNA molecules encoding delta-endotoxin transgenes can be purchased from American Type Culture Collection, Manassas, Va., for example, under ATCC Accession Nos. 40098, 67136, 31995, and 31998.

3. A lectin. See, for example, the disclosure by Van Damme, et al., Plant Mol. Biol., 24:25 (1994), who disclose the nucleotide sequences of several *Clivia miniata* mannose-binding lectin transgenes.

4. A vitamin-binding protein such as avidin. See, e.g., PCT Application No. US 93/06487. The application teaches the use of avidin and avidin homologues as larvicides against insect pests.

5. An enzyme inhibitor, for example, a protease or proteinase inhibitor, or an amylase inhibitor. See, for example, Abe, et al., J. Biol. Chem., 262:16793 (1987) (nucleotide sequence of rice cysteine proteinase inhibitor); Huub, et al., Plant Mol. Biol., 21:985 (1993) (nucleotide sequence of cDNA encoding tobacco proteinase inhibitor I); and Sumitani, et al., Biosci. Biotech. Biochem., 57:1243 (1993) (nucleotide sequence of *Streptomyces nitrosporeus* alpha-amylase inhibitor).

6. An insect-specific hormone or pheromone, such as an ecdysteroid and juvenile hormone, a variant thereof, a mimetic based thereon, or an antagonist or agonist thereof. See, for example, the disclosure by Hammock, et al., Nature, 344:458 (1990), of baculovirus expression of cloned juvenile hormone esterase, an inactivator of juvenile hormone.

7. An insect-specific peptide or neuropeptide which, upon expression, disrupts the physiology of the affected pest. For example, see the disclosures of Regan, J. Biol. Chem., 269:9 (1994) (expression cloning yields DNA coding for insect diuretic hormone receptor) and Pratt, et al., Biochem. Biophys. Res. Comm., 163:1243 (1989) (an allostatin is identified in *Diploptera puntata*). See also, U.S. Pat. No. 5,266,317 to Tomalski, et al., who disclose transgenes encoding insect-specific, paralytic neurotoxins.

8. An insect-specific venom produced in nature, by a snake, a wasp, etc. For example, see Pang, et al, Gene, 116:165 (1992), for disclosure of heterologous expression in plants of a transgene coding for a scorpion insectotoxic peptide.

9. An enzyme responsible for a hyper-accumulation of a monoterpene, a sesquiterpene, a steroid, hydroxamic acid, a phenylpropanoid derivative, or another non-protein molecule with insecticidal activity.

10. An enzyme involved in the modification, including the post-translational modification, of a biologically active molecule; for example, a glycolytic enzyme, a proteolytic enzyme, a lipolytic enzyme, a nuclease, a cyclase, a transaminase, an esterase, a hydrolase, a phosphatase, a kinase, a phosphorylase, a polymerase, an elastase, a chitinase, and a glucanase, whether natural or synthetic. See PCT Application No. WO 93/02197 in the name of Scott, et al., which discloses the nucleotide sequence of a callase transgene. DNA molecules which contain chitinase-encoding sequences can be obtained, for example, from the ATCC under Accession Nos. 39637 and 67152. See also, Kramer, et al., Insect Biochem. Mol. Biol., 23:691 (1993), who teach the nucleotide sequence of a cDNA encoding tobacco hornworm chitinase, and Kawalleck, et al., Plant Mol. Biol., 21:673 (1993), who provide the nucleotide sequence of the parsley ubi4-2 polyubiquitin transgene.

11. A molecule that stimulates signal transduction. For example, see the disclosure by Botella, et al., Plant Mol. Biol., 24:757 (1994), of nucleotide sequences for mung bean calmodulin cDNA clones, and Griess, et al., Plant Physiol., 104: 1467 (1994), who provide the nucleotide sequence of a maize calmodulin cDNA clone.

12. A hydrophobic moment peptide. See PCT Application No. WO 95/16776 (disclosure of peptide derivatives of tachyplesin which inhibit fungal plant pathogens) and PCT Application No. WO 95/18855 (teaches synthetic antimicrobial peptides that confer disease resistance).

13. A membrane permease, a channel former, or a channel blocker. For example, see the disclosure of Jaynes, et al., Plant Sci., 89:43 (1993), of heterologous expression of a cecropin-beta, lytic peptide analog to render transgenic tobacco plants resistant to *Pseudomonas solanacearum*.

14. A viral-invasive protein or a complex toxin derived therefrom. For example, the accumulation of viral coat proteins in transformed plant cells imparts resistance to viral infection and/or disease development effected by the virus from which the coat protein transgene is derived, as well as by related viruses. See Beachy, et al., Ann. Rev. Phytopathol., 28:451 (1990). Coat protein-mediated resistance has been conferred upon transformed plants against alfalfa mosaic virus, cucumber mosaic virus, tobacco streak virus, potato virus X, potato virus Y, tobacco etch virus, tobacco rattle virus, and tobacco mosaic virus. Id.

15. An insect-specific antibody or an immunotoxin derived therefrom. Thus, an antibody targeted to a critical metabolic function in the insect gut would inactivate an affected enzyme, killing the insect. See Taylor, et al., Abstract #497, Seventh Intl Symposium on Molecular Plant-Microbe Interactions, Edinburgh, Scotland (1994) (enzymatic inactivation in transgenic tobacco via production of single-chain antibody fragments).

16. A virus-specific antibody. See, for example, Tavladoraki, et al., Nature, 366:469 (1993), who show that transgenic plants expressing recombinant antibody transgenes are protected from virus attack.

17. A developmental-arrestive protein produced in nature by a pathogen or a parasite. Thus, fungal endo-alpha-1,4-D-polygalacturonases facilitate fungal colonization and plant nutrient released by solubilizing plant cell wall homo-alpha-1,4-D-galacturonase. See Lamb, et al., Bio/technology, 10:1436 (1992). The cloning and characterization of a transgene which encodes a bean endopolygalacturonase-inhibiting protein is described by Toubart, et al., Plant J., 2:367 (1992).

18. A developmental-arrestive protein produced in nature by a plant. For example, Logemann, et al., Bio/technology, 10:305 (1992), have shown that transgenic plants expressing the barley ribosome-inactivating transgene have an increased resistance to fungal disease.

Any disease or present resistance transgenes, including those exemplified above, can be introduced into a melon plant of the invention through a variety of means including but not limited to transformation and breeding.

B. Transgenes that Confer Resistance to an Herbicide:

Exemplary polynucleotides encoding polypeptides that confer traits desirable for herbicide resistance include acetolactate synthase (ALS) mutants that lead to herbicide resistance such as the S4 and/or Hra mutations ((resistance to herbicides including sulfonylureas, imidazolinones, triazolopyrimidines, pyrimidinyl thiobenzoates); glyphosate resistance (e.g., 5-enol-pyrovyl-shikimate-3-phosphate-synthase (EPSPS) transgene, including but not limited to those described in U.S. Pat. Nos. 4,940,935, 5,188,642, 5,633,435, 6,566,587, 7,674,598 as well as all related application; or the glyphosate N-acetyltransferase (GAT) transgene, described in Castle et al., Science, 2004, 304:1151-1154; and in U.S. Patent Application Publication Nos. 20070004912, 20050246798, and 20050060767)); glufosinate resistance (e.g., BAR; see e.g., U.S. Pat. No. 5,561,236); 2,4-D resistance (e.g., aryloxy alkanoate dioxygenase or AAD-1, AAD-12, or AAD-13), HPPD resistance (e.g., *Pseudomonas* HPPD) and PPO resistance (e.g., fomesafen, acifluorfen-sodium, oxyfluorfen, lactofen, fluthiacet-methyl, saflufenacil, flumioxazin, flumiclorac-pentyl, carfentrazone-ethyl, sulfentrazone,); a cytochrome P450 or variant thereof that confers herbicide resistance or tolerance to, inter alia, HPPD-inhibiting herbicides, PPO-inhibiting herbicides and ALS-inhibiting herbicides (U.S. Patent Application Publication No. 20090011936; U.S. Pat. Nos. 6,380,465; 6,121,512; 5,349,127; 6,649,814; and 6,300,544; and PCT International Publication No. WO 2007/000077); dicamba resistance (e.g., dicamba monoxygenase), and traits desirable for processing or process products such as high oil (e.g., U.S. Pat. No. 6,232,529); modified oils (e.g., fatty acid desaturase transgenes (U.S. Pat. No. 5,952,544; PCT International Publication No. WO 94/11516)); modified starches (e.g., ADPG pyrophosphorylases (AGPase), starch synthases (SS), starch branching enzymes (SBE), and starch debranching enzymes (SDBE)); and polymers or bioplastics (e.g., U.S. Pat. No. 5,602,321; beta-ketothiolase, polyhydroxybutyrate synthase, and acetoacetyl-CoA reductase (Schubert et al., J. Bacteriol., 1988, 170:5837-5847) facilitate expression of polyhydroxyalkanoates (PHAs)).

In embodiments, the polynucleotide encodes a polypeptide conferring resistance to an herbicide selected from glyphosate, sulfonylurea, imidazolinone, dicamba, glufosinate, phenoxy proprionic acid, L-phosphinothricin, cyclohexone, cyclohexanedione, triazine, and benzonitrile.

Any transgene conferring herbicide resistance, including those exemplified above, can be introduced into the melon plants of the invention through a variety of means including, but not limited to, transformation (e.g., genetic engineering techniques) and crossing.

C. Transgenes that Confer or Contribute to a Value-Added Trait:

1. Increased iron content, for example, by introducing into a plant a soybean ferritin transgene as described in Goto, et al., Acta Horticulturae., 521, 101-109 (2000).

2. Decreased nitrate content of leaves, for example, by introducing a transgene coding for a nitrate reductase. See, for example, Curtis, et al., Plant Cell Rep., 18:11, 889-896 (1999).

3. Increased sweetness of the fruit by introducing a transgene coding for monellin that elicits a flavor 100,000 times sweeter than sugar on a molar basis. See Penarrubia, et al., Bio/technology, 10:561-564 (1992).

4. Modified fatty acid metabolism, for example, by introducing into a plant an antisense sequence directed against stearyl- ACP desaturase to increase stearic acid content of the plant. See Knultzon, et al., PNAS, 89:2625 (1992).

5. Modified carbohydrate composition effected, for example, by introducing into plants a transgene coding for an enzyme that alters the branching pattern of starch. See Shiroza, et al., J. Bacteria, 170:810 (1988) (nucleotide sequence of *Streptococcus* mutants fructosyltransferase transgene); Steinmetz, et al., Mol. Gen. Genet., 20:220 (1985) (nucleotide sequence of *Bacillus subtilis* levansucrase transgene); Pen, et al., Bio/technology, 10:292 (1992) (production of transgenic plants that express *Bacillus licheniformis* alpha-amylase); Elliot, et al., Plant Mol. Biol., 21:515 (1993) (nucleotide sequences of tomato invertase transgenes); Sogaard, et al., J. Biol. Chem., 268:22480 (1993) (site-directed mutagenesis of barley alpha-amylase transgene); and Fisher, et al., Plant Physiol., 102:1045 (1993) (maize endosperm starch branching enzyme II).

Any transgene that confers or contributes a value-added trait, including those exemplified above, can be introduced into the melon plants of the invention through a variety of means including, but not limited to, transformation (e.g., genetic engineering techniques) and crossing.

D. Transgenes that Control Male-Sterility:

1. Introduction of a deacetylase transgene under the control of a tapetum-specific promoter and with the application of the chemical N-Ac-PPT. See, e.g., International Publication WO 01/29237.

2. Introduction of various stamen-specific promoters. See, e.g., International Publications WO 92/13956 and WO 92/13957.

3. Introduction of the barnase and the barstar transgenes. See, e.g., Paul, et al., Plant Mol. Biol., 19:611-622 (1992).

Any transgene that controls male sterility, including those exemplified above, can be introduced into the melon plants of the invention through a variety of means including, but not limited to, transformation (e.g., genetic engineering techniques) and crossing.

Methods for Plant Transformation

Numerous methods for plant transformation have been developed, including biological and physical, plant transformation protocols. See, for example, Miki, et al., "Procedures for Introducing Foreign DNA into Plants" in Methods in Plant Molecular Biology and Biotechnology, Glick and Thompson Eds., CRC Press, Inc., Boca Raton, pp. 67-88 (1993). In addition, expression vectors and in vitro culture methods for plant cell or tissue transformation and regeneration of plants are available. See, for example, Gruber, et al., "Vectors for Plant Transformation" in Methods in Plant Molecular Biology and Biotechnology, Glick and Thompson Eds., CRC Press, Inc., Boca Raton, pp. 89-119 (1993).

A. *Agrobacterium*-Mediated Transformation.

One method for introducing an expression vector into plants is based on the natural transformation system of *Agrobacterium*. See, for example, Horsch, et al., Science, 227:1229 (1985); Curtis, et al., Journal of Experimental Botany, 45:279, 1441-1449 (1994); Torres, et al., Plant Cell Tissue and Organ Culture, 34:3, 279-285 (1993); and Dinant, et al., Molecular Breeding, 3:1, 75-86 (1997). *A. tumefaciens* and *A. rhizogenes* are plant pathogenic soil bacteria which genetically transform plant cells. The Ti and Ri plasmids of *A. tumefaciens* and *A. rhizogenes*, respectively, carry genes responsible for genetic transformation of the plant. See, for example, Kado, C. I., Crit. Rev. Plant Sci., 10:1 (1991). Descriptions of *Agrobacterium* vector systems and methods for *Agrobacterium*-mediated transgene transfer are provided by Gruber, et al., supra, Miki, et al., supra, and Moloney, et al., Plant Cell Rep., 8:238 (1989). See also, U.S. Pat. No. 5,591,616 issued Jan. 7, 1997.

B. Direct Transgene Transfer.

Several methods of plant transformation collectively referred to as direct transgene transfer have been developed as an alternative to *Agrobacterium*-mediated transformation. A generally applicable method of plant transformation is microprojectile-mediated transformation wherein DNA is carried on the surface of microprojectiles measuring 1 micron to 4 micron. The expression vector is introduced into plant tissues with a biolistic device that accelerates the microprojectiles to speeds of 300 m/s to 600 m/s which is sufficient to penetrate plant cell walls and membranes. Russell, D. R., et al., Plant Cell Rep., 12 (3, January), 165-169 (1993); Aragao, F. J. L., et al., Plant Mol. Biol., 20 (2, October), 357-359 (1992); Aragao, F. J. L., et al., Plant Cell Rep., 12 (9, July), 483-490 (1993); Aragao, Theor. Appl. Genet., 93:142-150 (1996); Kim, J., Minamikawa, T., Plant Sci., 117:131-138 (1996); Sanford, et al., Part. Sci. Technol., 5:27 (1987); Sanford, J. C., Trends Biotech., 6:299 (1988); Klein, et al., Bio/technology, 6:559-563 (1988); Sanford, J. C., Physiol. Plant, 7:206 (1990); Klein, et al., Bio/technology, 10:268 (1992).

Another method for physical delivery of DNA to plants is sonication of target cells. Zhang, et al., Bio/technology, 9:996 (1991). Alternatively, liposome and spheroplast fusion have been used to introduce expression vectors into plants. Deshayes, et al., EMBO J., 4:2731 (1985) and Christou, et al., PNAS, 84:3962 (1987). Direct uptake of DNA into protoplasts using $CaCl_2$ precipitation, polyvinyl alcohol, or poly-L-ornithine has also been reported. Hain, et al., Mol. Gen. Genet., 199:161 (1985) and Draper, et al., Plant Cell Physiol., 23:451 (1982). Electroporation of protoplasts and whole cells and tissues have also been described. Saker, M., Kuhne, T., Biologia Plantarum, 40(4):507-514 (1997/98); Donn, et al., In Abstracts of VIIth International Congress on Plant Cell and Tissue Culture IAPTC, A2-38, p. 53 (1990); D'Halluin, et al., Plant Cell, 4:1495-1505 (1992); and Spencer, et al., Plant Mol. Biol., 24:51-61 (1994). See also Chupean, et al., Bio/technology, 7:5, 503-508 (1989).

Following transformation of plant target tissues, expression of the above-described selectable marker transgenes allows for preferential selection of transformed cells, tissues and/or plants, using regeneration and selection methods now well known in the art.

The foregoing methods for transformation would typically be used for producing a transgenic melon line. The transgenic melon line could then be crossed with another (non-transformed or transformed) line in order to produce a new transgenic melon line. Alternatively, a genetic trait that has been engineered into a particular plant cultivar using the foregoing transformation techniques could be introduced into another line using traditional breeding (e.g., backcrossing) techniques that are well known in the plant breeding arts. For example, a backcrossing approach could be used to move an engineered trait from a public, non-elite inbred line into an elite inbred line, or from an inbred line containing a foreign transgene in its genome into an inbred line or lines which do not contain that transgene. As used herein, "crossing" can refer to a simple X by Y cross, or the process of backcrossing, depending on the context.

Gene Conversions.

When the term "melon plant" or "cantaloupe plant" is used in the context of the present invention, this also includes any gene conversions of that plant or variety. The term "gene converted plant" as used herein refers to those melon or cantaloupe plants that are developed by backcrossing, genetic engineering, or mutation, wherein essentially all of the desired morphological and physiological characteristics of a variety (e.g., non-climacteric fruit ripening and/or fruit having a firm flesh and/or fruit having high soluble solids) are recovered in addition to the one or more transgenes transferred into the variety via the backcrossing technique, genetic engineering, or mutation. Backcrossing methods can be used with the present invention to improve or introduce a characteristic into the variety. The term "backcrossing" as used herein refers to the repeated crossing of a hybrid progeny back to the recurrent parent, e.g., backcrossing 1, 2, 3, 4, 5, 6, 7, 8, 9, or more times to the recurrent parent. The parental plant that contributes the transgene for the desired characteristic is termed the "nonrecurrent" or "donor parent." This terminology refers to the fact that the nonrecurrent parent is used one time in the backcross protocol and therefore does not recur. The parental plant to which the transgene or transgenes from the nonrecurrent parent are transferred is known as the recurrent parent as it is used for several rounds in the backcrossing protocol. Poehlman & Sleper (1994) and Fehr (1993). In a typical backcross protocol, the original variety of interest (recurrent parent) is crossed to a second variety (nonrecurrent parent) that carries the transgene of interest to be transferred. The resulting progeny from this cross are then crossed again to the recurrent parent and the process is repeated until a plant is obtained wherein essentially all of the desired morphological and physiological characteristics of the recurrent parent are recovered in the converted plant, in addition to the transferred transgene from the nonrecurrent parent.

Many gene traits have been identified that are not regularly selected in the development of a new line but that can be improved by backcrossing techniques. Gene traits may or may not be transgenic. Examples of these traits include, but are not limited to, male sterility, modified fatty acid metabolism, modified carbohydrate metabolism, herbicide resistance, pest or disease resistance (e.g., resistance to bacterial, fungal, or viral disease), insect resistance, enhanced nutritional quality, increased sweetness, increased flavor, improved ripening control, improved salt tolerance, industrial usage, yield stability, and yield enhancement. These genes are generally inherited through the nucleus.

Tissue Culture.

Further reproduction of melon plants variety can occur by tissue culture and regeneration. Tissue culture of various tissues of melon and regeneration of plants therefrom is well known and widely published. For example, reference may be had to Teng, et al., HortScience, 27:9, 1030-1032 (1992); Teng, et al., HortScience, 28:6, 669-1671 (1993); Zhang, et al., Journal of Genetics and Breeding, 46:3, 287-290 (1992); Webb, et al., Plant Cell Tissue and Organ Culture, 38:1, 77-79 (1994); Curtis, et al., Journal of Experimental Botany, 45:279, 1441-1449 (1994); Nagata, et al., Journal for the American Society for Horticultural Science, 125:6, 669-672 (2000); and Ibrahim, et al., Plant Cell Tissue and Organ Culture, 28(2), 139-145 (1992). It is clear from the literature that the state of the art is such that these methods of obtaining plants are routinely used and have a very high rate of success. Thus, another aspect of this invention is to provide cells which upon growth and differentiation produce melon plants having desired characteristics of cantaloupe cultivars ME007 and ME009 (e.g., non-climacteric fruit ripening and/or fruit having a firm flesh and/or high soluble solids). Optionally, melon plants can be regenerated from the tissue culture of the invention comprising all the physiological and morphological characteristics of cantaloupe cultivars ME007 and ME009.

As used herein, the term "tissue culture" indicates a composition comprising isolated cells of the same or a different type or a collection of such cells organized into parts of a plant. Exemplary types of tissue cultures are protoplasts, calli, meristematic cells, and plant cells that can generate tissue culture that are intact in plants or parts of plants, such as leaves, pollen, embryos, roots, root tips, anthers, pistils, flowers, seeds, petioles, suckers, and the like. Means for preparing and maintaining plant tissue culture are well known in the art. By way of example, a tissue culture comprising organs has been used to produce regenerated plants. U.S. Pat. Nos. 5,959,185, 5,973,234, and 5,977,445 describe certain techniques.

Additional Breeding Methods.

This invention is also directed to methods for producing a melon plant by crossing a first parent melon plant with a second parent melon plant wherein the first or second parent melon plant is a plant of cantaloupe cultivar ME007 or ME009. Further, both first and second parent melon plants can come from cantaloupe cultivar ME007 or ME009. Thus, any of the following exemplary methods using cantaloupe cultivar ME007 or ME009 are part of this invention: selfing, backcrosses, hybrid production, crosses to populations, and the like. All plants produced using cantaloupe cultivar ME007 or ME009 as at least one parent are within the scope of this invention, including those developed from melon plants derived from cantaloupe cultivar ME007 or ME009. Advantageously, cantaloupe cultivars ME007 and ME009 can be used in crosses with other, different, melon plants to produce the first generation ($F_1$) melon hybrid seeds and plants with desirable characteristics. The cultivars of the invention can also be used for transformation where exogenous transgenes are introduced and expressed by the cultivars of the invention. Genetic variants created either through traditional breeding methods or through transformation of the cultivars of the invention by any of a number of protocols known to those of skill in the art are intended to be within the scope of this invention.

Those skilled in the art will appreciate that cantaloupe melons can be readily crossed with other melons, e.g., another *C. melo* melon including without limitation honeydew, Tuscan, Piel de Sapo, Yellow Canary, Japanese, Charentais, Galia, Amarello, Kirkagak, Hamy, Ananas, Oriental, and the like. Thus, the methods of the invention encompass crosses between cantaloupe cultivars ME007 and ME009, and progeny and derivatives thereof, with other melons including cantaloupe melons or any other melon type.

The following describes exemplary breeding methods that may be used with cantaloupe cultivar ME007 and ME009 in the development of further melon plants. One such embodiment is a method for developing cantaloupe cultivar ME007 and ME009 progeny melon plants in a melon plant breeding program comprising: obtaining a plant, or a part thereof, of cantaloupe cultivar ME007 or ME009, utilizing said plant or plant part as a source of breeding material, and selecting a cantaloupe cultivar ME007 or ME009 progeny plant with molecular markers in common with cantaloupe cultivar ME007 or ME009 and/or with morphological and/or physiological characteristics described herein (e.g., non-climacteric fruit ripening and/or producing fruit with a firm flesh and/or fruit having a high total soluble solids). In representative embodiments, the progeny plant has at least 3, 4, 5, 6, 7, 8. 9, 10 or more of the morphological and physiological characteristics of cantaloupe cultivars ME007 or ME009, respectively (e.g., as described in Tables 1 to 5), or even of all the morphological and physiological characteristics of cantaloupe cultivars ME007 or ME009, respectively, so that said progeny melon plant is not significantly different for said traits than cantaloupe cultivar ME007 or ME009, respectively, as determined at the 5% significance level when grown in the same environmental conditions; optionally, with the presence of one or more desired additional traits (e.g., male sterility, disease resistance, pest or insect resistance, herbicide resistance, and the like). Breeding steps that may be used in the breeding program include pedigree breeding, backcrossing, mutation breeding, and recurrent selection. In conjunction with these steps, techniques such as RFLP-enhanced selection, genetic marker enhanced selection (for example, SSR markers), and the making of double haploids may be utilized.

Another representative method involves producing a population of cantaloupe cultivar ME007 or ME009 progeny melon plants, comprising crossing a cantaloupe cultivar of the invention with another melon plant, thereby producing a population of melon plants, which, on average, derive 50% of their alleles from cantaloupe cultivar ME007 or ME009, respectively. A plant of this population may be selected and repeatedly selfed or sibbed with a melon plant resulting from these successive filial generations. One embodiment of this invention is the melon plant produced by this method and that has obtained at least 50% of its alleles from cantaloupe cultivar ME007 or ME009.

One of ordinary skill in the art of plant breeding would know how to evaluate the traits of two plant varieties to determine if there is no significant difference between the two traits expressed by those varieties. For example, see Fehr and Walt, Principles of Cultivar Development, pp. 261-286 (1987). Thus the invention includes cantaloupe cultivar ME007 and ME009 progeny melon plants characterized by non-climacteric fruit ripening and/or a fruit having a firm flesh and/or a fruit with high soluble solids. In embodiments, the invention encompasses progeny plants having a combination of at least 2, 3, 4, 5 or 6 characteristics as described herein for cantaloupe cultivar ME007 or ME009, so that said progeny melon plant is not significantly different for said traits than cantaloupe cultivar ME007 or ME009, respectively, as determined at the 5% significance level when grown in the same environmental conditions. Using techniques described herein and those known in the art, molecular markers may be used to identify said progeny plant as progeny of cantaloupe cultivar ME007 and ME009. Mean trait values may be used to determine whether trait differences are significant, and optionally the traits are measured on plants grown under the same environmental conditions.

Progeny of cantaloupe cultivar ME007 and ME009 may also be characterized through their filial relationship with cantaloupe cultivar ME007 and ME009, respectively, as for example, being within a certain number of breeding crosses of cantaloupe cultivar ME007 and ME009. A breeding cross is a cross made to introduce new genetics into the progeny, and is distinguished from a cross, such as a self or a sib cross, made to select among existing genetic alleles. The lower the number of breeding crosses in the pedigree, the closer the relationship between cantaloupe cultivars ME007 or ME009 and its progeny. For example, progeny produced by the methods described herein may be within 1, 2, 3, 4, 5 or more breeding crosses of cantaloupe cultivars ME007 or ME009.

Those skilled in the art will appreciate that any of the traits described above with respect to plant transformation methods can be introduced into a plant of the invention (e.g., cantaloupe cultivars ME007 and ME009, and hybrid melon plants and other melon plants derived therefrom) using breeding techniques.

DEPOSIT

Applicants have made a deposit of at least 2500 seeds of cantaloupe varieties ME007 and ME009 with the American Type Culture Collection (ATCC), University Boulevard, Manassas, Va., 20110-2209 U.S.A. under ATCC Deposit Nos. PTA-121092 and PTA-121093, respectively, on Mar. 18, 2014. These deposits of cantaloupe varieties ME007 and ME009 will be maintained in the ATCC depository, which is a public depository, for a period of 30 years, or 5 years after the most recent request, or for the effective life of the patent, whichever is longer, and will be replaced if any of the deposited seed becomes nonviable during that period. Additionally, Applicants have satisfied all the requirements of 37 C.F.R. §§1.801-1.809, including providing an indication of the viability of the samples. Access to these deposits will be made available during the pendency of this application to the Commissioner upon request. Upon the issuance of a patent on the varieties, the varieties will be irrevocably and without restriction released to the public by providing access to the deposits of at least 2500 seeds of the varieties with the ATCC. Applicants impose no restrictions on the availability of the deposited material from the ATCC; however, Applicants have no authority to waive any restrictions imposed by law on the transfer of biological material or its transportation in commerce. Applicants do not waive any infringement of its rights granted under this patent or under the Plant Variety Protection Act (7 USC §2321 et seq.).

The foregoing invention has been described in detail by way of illustration and example for purposes of clarity and understanding. However, it will be apparent that certain changes and modifications such as single gene modifications and mutations, somaclonal variants, variant individuals selected from large populations of the plants of the instant inbred and the like may be practiced within the scope of the invention. Thus, although the foregoing invention has been described in some detail in this document, it will be obvious that changes and modifications may be practiced within the scope of the invention.

What is claimed is:

1. A seed of a cantaloupe selected from cantaloupe cultivar ME007 or ME009, a sample of seed having been deposited under ATCC Accession Nos. PTA-121092 and PTA-121093, respectively.

2. A plant of cantaloupe cultivar ME007 or ME009, a sample of seed of said cantaloupe plant having been deposited under ATCC Accession Nos. PTA-121092 and PTA-121093, respectively.

3. A cantaloupe plant, or a part thereof, having all the physiological and morphological characteristics of the cantaloupe plant of claim 2.

4. Pollen of the plant of claim 2.

5. An ovule of the plant of claim 2.

6. A tissue culture of regenerable cells of the plant of claim 2.

7. The tissue culture of claim 6, wherein the cells are:
   (a) embryos, meristem, leaves, pollen, cotyledons, hypocotyls, roots, root tips, anthers, flowers, pistils, ovules, seed, shoots, stems, stalks, petioles, pith and/or capsules; or
   (b) callus or protoplasts derived from the cells of (a).

8. A cantaloupe plant regenerated from the tissue culture of claim 6.

9. A part of the cantaloupe plant of claim 2.

10. Fruit from the plant of claim 2.

11. Flesh of the fruit of claim 10.

12. A processed product from the fruit of claim 10.

13. A method of producing cantaloupe seed, the method comprising crossing the plant of claim 2 with itself or a second melon plant.

14. A seed produced by the method of claim 13.

15. A plant produced by growing the seed of claim 14.

16. A method for producing a seed of a melon plant derived from the plant of claim 2, the method comprising:
(a) crossing a melon plant of cantaloupe cultivar ME007 or ME009 with a second melon plant, a sample of seed of said cantaloupe plant having been deposited under ATCC Accession Nos. PTA-121092 and PTA-121093, respectively; and
(b) allowing seed of a melon plant derived from cantaloupe cultivar ME007 or ME009 to form.

17. The method of claim 16, further comprising:
(c) selfing the plant grown from the melon seed derived from cantaloupe cultivar ME007 or ME009 or crossing it to a second melon plant to yield additional melon seed derived from cantaloupe ME007 or ME009;
(d) growing plants from the additional melon seed derived from cantaloupe cultivar ME007 or ME009 of step (c) to yield additional melon plants derived from cantaloupe ME007 or ME009; and
(e) repeating (c) and (d) to generate further derived melon plants.

18. A seed produced by the method of claim 16.

19. A plant produced by growing the seed of claim 18.

20. A method of producing cantaloupe fruit, the method comprising:
(a) obtaining the plant of claim 2, wherein the plant has been cultivated to maturity; and
(b) collecting fruit from the plant.

21. A method of vegetatively propagating the plant of claim 2, the method comprising:
(a) collecting tissue capable of being propagated from a plant of cantaloupe cultivar ME007 or ME009, a sample of seed of said cantaloupe plant having been deposited under ATCC Accession Nos. PTA-121092 and PTA-121093, respectively;
(b) cultivating the tissue to obtain proliferated shoots; and
(c) rooting the proliferated shoots to obtain rooted plantlets.

22. The method of claim 21, further comprising growing plants from the rooted plantlets.

23. Plantlets obtained by the method of claim 21.

24. A method of producing a plant derived from the plant of claim 2 and comprising a desired added trait, the method comprising:
(a) crossing a first plant of cantaloupe cultivar ME007 or ME009, a sample of seed of said cantaloupe plant having been deposited under ATCC Accession Nos. PTA-121092 and PTA-121093 and respectively, with a second melon plant that comprises a desired added trait to produce F1 progeny;
(b) selecting an F1 progeny that comprises the desired added trait;
(c) crossing the selected F1 progeny with the first plant of cantaloupe cultivar ME007 or ME009 to produce backcross progeny;
(d) selecting backcross progeny comprising the desired added trait and the physiological and morphological characteristic of the first plant of cantaloupe cultivar ME007 or ME009; and
(e) repeating steps (c) and (d) one or more times in succession to produce a plant derived from cantaloupe cultivar ME007 or ME009 comprising a desired added trait.

25. The method of claim 24, wherein the desired added trait is male sterility, pest resistance, insect resistance, disease resistance, herbicide resistance, or any combination thereof.

26. A melon plant produced by the method of claim 24, wherein the melon plant has the desired added trait.

27. Seed of the plant of claim 26.

28. A method of producing a plant of cantaloupe cultivar ME007 or ME009 comprising a desired added desired trait, the method comprising introducing a transgene conferring the desired trait into the plant of claim 2.

29. A melon plant produced by the method of claim 28, wherein the melon plant has the desired added trait.

30. Seed of the plant of claim 29.

\* \* \* \* \*